(12) United States Patent
Al Ahmad et al.

(10) Patent No.: US 10,401,139 B2
(45) Date of Patent: Sep. 3, 2019

(54) SELF-BIASED SENSING DEVICE AND METHODS OF FABRICATING AND OPERATING SAME

(71) Applicant: United Arab Emirates University, Al Ain (AE)

(72) Inventors: Mahmoud F. Y. Al Ahmad, Al Ain (AE); Areen Abdellah Romi Allataifeh, Al Ain (AE)

(73) Assignee: United Arab Emirates University, Al Ain (AE)

( * ) Notice: Subject to any disclaimer, the term of this patent is extended or adjusted under 35 U.S.C. 154(b) by 359 days.

(21) Appl. No.: 15/403,042

(22) Filed: Jan. 10, 2017

(65) Prior Publication Data
US 2018/0195921 A1    Jul. 12, 2018

(51) Int. Cl.
| | |
|---|---|
| H01L 41/047 | (2006.01) |
| G01B 7/16 | (2006.01) |
| A61B 5/00 | (2006.01) |
| G01L 9/00 | (2006.01) |
| A61B 5/021 | (2006.01) |

(52) U.S. Cl.
CPC .................. *G01B 7/18* (2013.01); *A61B 5/00* (2013.01); *A61B 5/02141* (2013.01); *G01B 7/16* (2013.01); *G01L 9/008* (2013.01); *G01L 9/0042* (2013.01); *H01L 41/047* (2013.01); *A61B 2560/0214* (2013.01)

(58) Field of Classification Search
CPC .................................................... H01L 41/047
USPC ................. 310/365, 366; 324/109
See application file for complete search history.

(56) References Cited

U.S. PATENT DOCUMENTS 3,351,786 A    11/1967    Muller et al.

OTHER PUBLICATIONS

Alpuim, P., et al., "Piezoresistive Silicon Thin Film Sensor Array for Biomedical Applications." Thin Solid Films, 2011, vol. 519, pp. 4574-4577.
Baccarani, Giorgio, et al., "Generalized Scaling Theory and Its Application to a 1/4 Micrometer MOSFET Design." IEEE Transactions on Electron Devices, 1984, vol. ED-31, No. 4, pp. 452-462.

(Continued)

*Primary Examiner* — Derek J Rosenau
(74) *Attorney, Agent, or Firm* — Fitch, Even, Tabin & Flannery LLP (57) ABSTRACT

A sensing device, a method for fabrication thereof, and a method for operating the same are disclosed. The sensing device includes an upper harvester having a piezoelectric (PE) thin film layer, a pressure sensor having a first metallization layer forming a source region and a drain region, a piezoresistive (PR) thin film layer that provides a channel region permitting passage of charge carriers between the source region and the drain region, a second metallization layer forming a gate electrode and regulating flow of the charge carriers through the piezoelectric thin film layer in response to a strain on the PE thin film layer, and an insulating layer disposed between the PR thin film layer and the second metallization layer. In other embodiments, the device includes a lower harvesting including a PE thin film layer for harvesting electrical energy from the stress of a mechanical load on the device.

20 Claims, 8 Drawing Sheets
(5 of 8 Drawing Sheet(s) Filed in Color)

(56) References Cited

OTHER PUBLICATIONS

Barlian, A. Alvin, et al., "Review: Semiconductor Piezoresistance for Microsystems." Proceedings of the IEEE Institute of Electrical and Electronics Engineers, Author manuscript, available Mar. 1, 2010 (91 pages).

Haensch, W., et al., "Silicon CMOS Devices Beyond Scaling." IBM Journal of Research & Development, vol. 50, No. 4/5, Jul./Sep. 2006, pp. 339-361.

Hu, Youfan, et al., "Recent Progress in Piezoelectric Nanogenerators As a Sustainable Power Source in Self-Powered Systems and Active Sensors." Nano Energy, 2015, <http://dx.doi.org/10.1016/j.nanoen.2014.11.038>, 12 pages.

Jain, Puneet Kumar, et al., "Heart Monitoring Systems—A Review." Computers in Biology and Medicine, 2014, vol. 54, pp. 1-13.

Li, Fei, et al., "Composition and Phase Dependence of the Intrinsic and Extrinsic Piezoelectric Activity of Domain Engineered $(1-x)Pb(Mg_{1/3}Nb_{2/3})O_3-xPbTiO_3$ Crystals." Journal of Applied Physics, 2010, vol. 108, pp. 034106-1 to 034106-9.

McEniery, Carmel M., et al., "Central Blood Pressure: Current Evidence and Clinical Importance." European Heart Journal, 2014, vol. 35, pp. 1719-1725b (9 pages).

Newns, Dennis M., et al., "High Response Piezoelectric and Piezoresistive Materials for Fast, Low Voltage Switching: Simulation and Theory of Transduction Physics at the Nanometer-Scale." Advanced Materials, 2012, vol. 24, pp. 3672-3677.

Park, Seung-Eek, et al., "Ultrahigh Strain and Piezoelectric Behavior in Relaxor Based Ferroelectric Single Crystals." Journal of Applied Physics, 1997, vol. 82, No. 4, pp. 1804-1811.

Safar, Michel E., et al., "Central Pulse Pressure and Mortality in End-Stage Renal Disease." Hypertension, Mar. 2002, pp. 735-738.

Shi, Changzhi, et al., "Piezoresistive Sensitivity, Linearity and Resistance Time Drift of Polysilicon Nanofilms with Different Deposition Temperatures." Sensors, 2009, vol. 9, pp. 1141-1166.

Takazawa, Kenji, et al., "Relationship between Radial and Central Arterial Pulse Wave and Evaluation of Central Aortic Pressure using the Radial Arterial Pulse Wave." Hypertension Research, 2007, vol. 30, No. 3, pp. 219-228.

Yu, Hua, et al., "A Vibration-Based MEMS Piezoelectric Energy Harvester and Power Conditioning Circuit." Sensors, 2014, vol. 14, pp. 3323-3341.

Yu, Huiyang, et al., "Design and Application of a High Sensitivity Piezoresistive Pressure Sensor for Low Pressure Conditions." Sensors, 2015, vol. 15, pp. 22692-22704.

«SELF-BIASED SENSING DEVICE AND METHODS OF FABRICATING AND OPERATING SAME»

TECHNICAL FIELD

This invention relates generally to a sensing device and more particularly, to a self-biased sensing device and methods of fabricating and operating same.

BACKGROUND

Harvesting energy from ambient vibrations to power devices is a promising way to rid them of power cables and batteries as well as decrease their power consumption and size. There has been an increased use of piezoelectric and piezoresistive materials in making of micro-harvesters. Micro-harvesters find their main application either as independent power sources or as active sensors.

Micro-electromechanical systems (MEMS) sensors convert applied pressure to electrical energy by capacitive and piezoresistive sensing mechanisms. Piezoresistive sensors have DC input, simple conditioning circuits and higher output in comparison to capacitive sensors. Piezoresistive devices include PMOS and NMOS field effect transistors, diodes, and simple p-type and n-type resistors.

Piezoelectric transistors PET have been produced in the art in which piezoelectric PE and piezoresistive PR material are used. PET generally is based on modulating resistance of a PR element with a PE element. That is, the PR element is programmable based on displacement of the PE element. The PET may be used as a switch device, for example, based on modulating the PR element from a low to a high resistive state or visa versa. In such PET devices, an electric field is applied to the PE element along the same direction as the resulting displacement of the PE element. Therefore, the piezoelectric material is electrically manipulated by use of an external power source to allow for electrically controlling the piezoresistor in the different devices.

There is a desire in the field for the development of sensors and sensing techniques to improve utilizing energy of surrounding sources and generate good quality sensory data in a cost efficient and durable fashion using easily accessible probing systems.

SUMMARY OF THE INVENTION

The current disclosure has several aspects. In one aspect of the invention, a self-biasing sensor is provided. The sensor includes an upper harvester and a pressure sensor. The upper harvester has a piezoelectric thin film layer. The pressure sensor is composed of the following layers: a first metallization layer forming at least a drain region and a source region; a piezoresistive thin film layer for providing a channel region permitting passage of charge carriers between the source region and the drain region; a second metallization layer forming a gate electrode, where the gate electrode is in electrical communication with the piezoelectric thin film layer of the upper harvester; and an insulator disposed intermediate the piezoresistive thin film layer and the second metallization layer, where the insulator insulates the piezoresistive thin film layer from the second metallization layer. The gate electrode in the device is in electrical communication with one of the drain region and the source region and the other one of the drain region and the source region is grounded. The gate electrode also facilitate regulation of a flow of charge carriers through the piezoelectric thin film layer of the upper harvester. Furthermore, the flow of charge carriers is modulated in response to a strain in the piezoelectric thin film layer.

The different layers of the device are formed in a vertical integration structure, where the piezoelectric thin film layer of the upper harvester is in a plane substantially perpendicular to a direction of the applied stress on the sensor and the first metallization layer and the second metallization layer are substantially parallel to the piezoelectric thin film layer of the upper harvester.

In another embodiment of the self-biasing sensor, the self-biasing sensor further includes a lower harvester having a piezoelectric thin firm layer for harvesting electrical energy in response to a strain in the piezoelectric thin film layer of the lower harvester and storing the harvested electrical energy in an energy storage unit.

In a related embodiment, the lower harvester and the upper harvester are disposed substantially parallel to one another in a plane substantially perpendicular to a direction of the applied strain on the device.

In another embodiment of the self-biasing sensor, the first metallization layer is disposed to form an interdigitated structure forming a plurality of pairs of source and drain electrodes.

In a related embodiment, the electrical current flowing across the source and the drain electrode is cumulative of individual electrical currents flowing between individual pairs of source and drain electrodes.

In another embodiment of the self-biasing sensor, the first metallization layer is disposed to form a fractal structure forming a plurality of pairs of source and drain electrodes.

In a related embodiment of the self-biasing sensor, the electrical current flowing across the source and the drain regions is cumulative of individual electrical currents flowing between individual pairs of source and drain electrodes.

In another embodiment of the self-biasing sensor, the second metallisation layer is disposed to form a fractal structure of the gate electrode.

In another embodiment of the self-biasing sensor, the gate electrode of the second metallisation layer is a floating gate.

In another embodiment of the self-biasing sensor, the source region and the drain region are arranged to form Ohmic contacts with the piezoresistive thin film layer.

A second aspect of the invention describes a method of forming a self-biasing sensor, the method includes the steps of providing an upper harvester forming a piezoelectric thin film layer; providing a first metallization layer forming at least a source region and at least a drain region; providing a piezoresistive thin film layer as a channel region permitting passage of charge carriers between the source region and the drain region; providing a second metallization layer forming a gate electrode, the gate electrode in electrical communication with the piezoelectric thin film layer of the upper harvester; providing an insulator disposed intermediate the piezoresistive thin film layer and the second metallization layer. The first metallization layer, the piezoresistive thin film layer, the second metallization layer and the insulator are vertically integrated to form a pressure sensor. The gate electrode facilitates regulation of a flow of charge carriers through the piezoelectric thin film layer of the upper harvester, and also the flow of charge carriers is modulated in response to a strain in the piezoelectric thin film layer.

In another embodiment, the method further comprising: forming a lower harvester having a piezoelectric thin firm layer for harvesting electrical energy in response to a strain in the piezoelectric thin film layer of the lower harvester and storing the harvested electrical energy in an energy storage unit.

In a related embodiment, the source region and the drain region are coplanar, the piezoelectric thin film layer is substantially perpendicular to the axis along which the strain is applied, and both the pressure sensor and the piezoelectric thin film layer of the lower harvester are substantially parallel to the piezoelectric thin film of the upper harvester.

A third aspect of the invention describes a method of operating a self-biased sensor, the self-biasing sensor comprising: an upper harvester having a piezoelectric thin film layer; and a pressure sensor comprising: a first metallization layer forming at least a drain region and a source region; a piezoresistive thin film layer for providing a channel region permitting passage of charge carriers between the source region and the drain region; a second metallization layer forming a gate electrode, the gate electrode in electrical communication with the piezoelectric thin film layer of the upper harvester; and an insulator disposed intermediate the piezoresistive thin film layer and the second metallization layer, the insulator insulating the piezoresistive thin film layer from the second metallization layer, the gate electrode is in electrical communication with one of the drain region and the source region and the other one of the drain region and the source region is grounded, and the gate electrode facilitates regulation of a flow of charge carriers through the piezoelectric thin film layer of the upper harvester, and the flow of charge carriers is modulated in response to a strain in the piezoelectric thin film layer. The method includes the steps of: coupling a source of mechanical load to the self-biasing sensor, the source of mechanical load applies a mechanical stress to the self-biasing sensor, the mechanical stress affecting the piezoelectric layer of the upper harvester and the piezoresistive layer of the pressure sensor; and generating and output current and voltage based on the applied mechanical stress, where the generated output current and voltage are sufficient to operate the self-biasing sensor without use of an external power source.

In a related embodiment of the method, the mechanical stress is associated with mechanical movement of a part of a person's body resulting from at least cardiac activity of the person and the method further includes the step of monitoring the cardiac activity of the person based on the generated output current and voltage.

In a related embodiment of the method, the method further includes: providing a lower harvester having a piezoelectric thin firm layer for harvesting electrical energy in response to a strain in the piezoelectric thin film layer of the lower harvester and storing the harvested electrical energy in an energy storage unit.

In a related embodiment of the method, the lower harvester and the upper harvester are disposed substantially parallel to one another in a plane substantially perpendicular to a direction of the applied strain.

In a related embodiment of the method, the method further includes the steps of: coupling a source of mechanical load to the self-biasing sensor, the source of mechanical load applies a mechanical stress to the self-biasing sensor, the mechanical stress straining the piezoelectric layer of the upper harvester, the piezoelectric thin film layer of the lower harvester and the piezoresistive layer of the pressure sensor; and generating an output current and voltage based on the applied mechanical stress, where the generated output current and voltage are sufficient to operate the self-biasing sensor without use of an external power source.

In a related embodiment of the method, the method further includes: using the electrical energy stored in the energy storage unit to trigger the pressure sensor and where the output current and voltage generated are based at least in part on the electrical energy used.

Other aspects of the invention will be apparent as will be shown in the detailed description of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DEATAILED DESCRIPTION

Throughout the following description specific details are set forth in order to provide a more thorough understanding to persons skilled in the art. However, well known elements may not have been shown or described in detail to avoid unnecessarily obscuring the disclosure. The following description of examples of the technology is not intended to be exhaustive or to limit the system to the precise forms of any example embodiment. Accordingly, the description and drawings are to be regarded in an illustrative, rather than a restrictive, sense.

This invention presents a sensing device and methods of fabricating and operating the sensing device, where the sensing device works on the principles of piezoelectricity and piezoresistivity to increase durability of the sensing device and facilitate use of such device in a wide verity of applications including in the medical field.

Piezoelectric based transducers technology could convert one form of energy into another. They have a range of uses, particularly as sensors. The piezoelectric effect refers to the phenomenon by which electrical polarization occurs in certain crystal materials upon application of an external source of mechanical nature. It has been used in thousands of sensing applications. These applications range from infrared sensors, stress gauges, and vibration detectors. The piezoelectric materials have also been used in nano-scale sensing devices. The use of piezoelectric components can be quite advantageous, since the piezoelectric components would need fewer parts to fulfill the desired functionality.

Piezoresistivity is the phenomenon by which a change in electrical resistance of a material is observed upon being subjected to any form of external stress. This change in the resistance value due to the applied stress is a function of the geometry of the device and resistivity changes. For piezoresistive sensing, both p-type and n-type silicon materials are used. This effect is utilized by the device to provide an output current corresponding to the applied stress input to the device.

The present invention describes a sensor device and method of fabricating and operating same in which an output current and voltage are generated under mechanical stress and without the use of an external power source to operate the sensor device.

Figure 1:
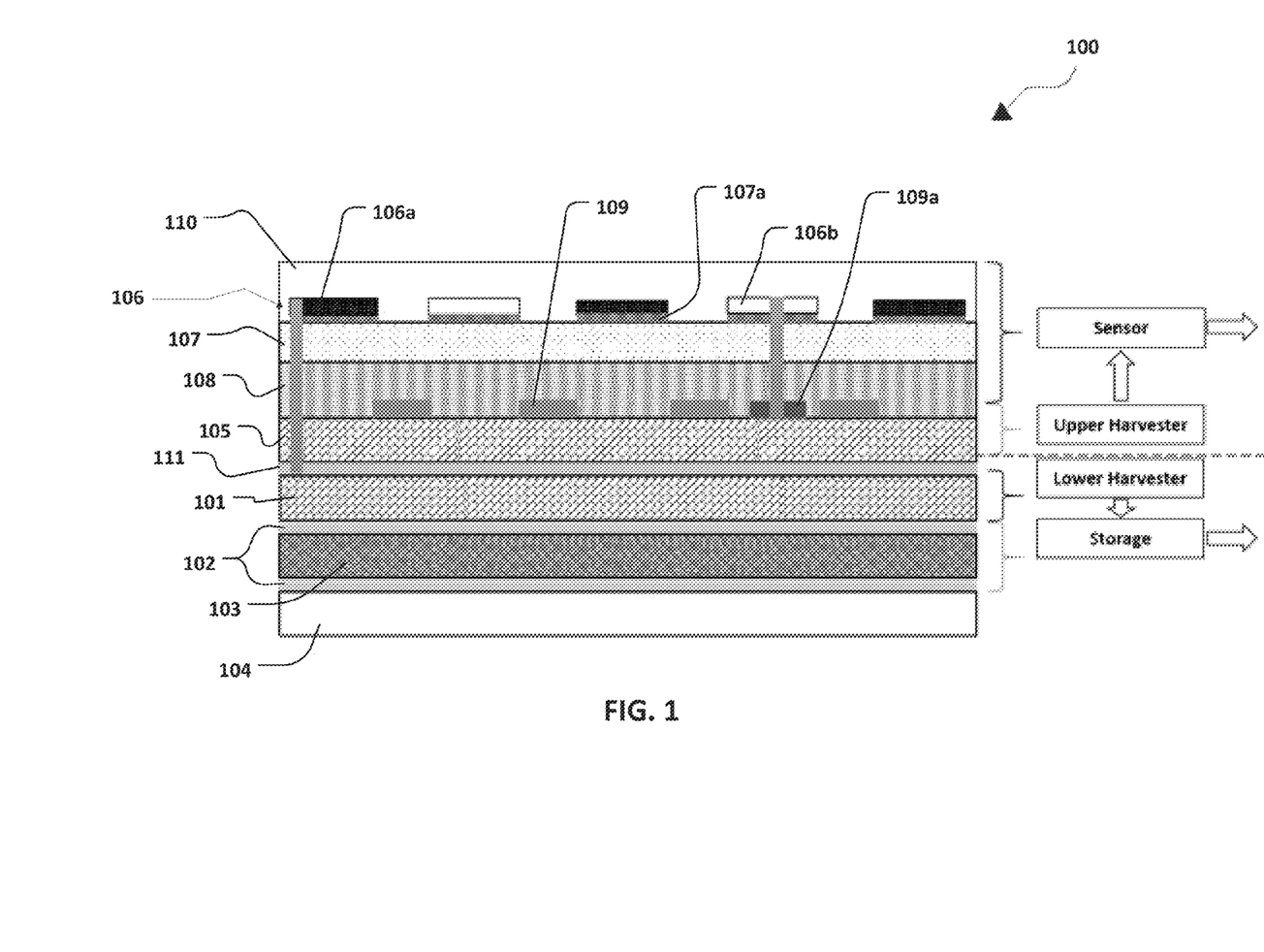
FIG. 1 shows a cross-sectional view of a sensor device according to an exemplary embodiment of the present invention.

Referring to FIG. 1, a cross-sectional view of a sensing device 100 is illustrated in accordance with an exemplary embodiment of the present invention.

Sensing device 100 includes an upper harvester, a lower harvester and a pressure sensor formed in a vertical integration configuration. The lower harvester comprises a piezoelectric thin film layer 101 in electrical communication with charge storage unit which has a capacitor formed from a high K/or composite polymer electrolyte material 103, 403 (in FIG. 4) positioned between two metal layers 102, 402 (in FIG. 4). A passive layer 104, 404 (in FIG. 4) is coupled to the capacitor and acts as a protecting layer and to enhance electrical characteristics of the device.

By way of non-limiting examples, Silicon_100 may be used in some embodiments to form the piezoelectric thin film layer 101. In other embodiments, the thin film piezoelectric layer 101 may be formed using Zinc Oxide (ZnO). It is to be understood that other materials known in the art, that may respond to vibrations by generating AC signal, may be used to form the thin film piezoelectric layer in the lower harvester. The piezoelectric layer 101 is considered to be the largest in width among the other layers in the device. By way of non-limiting example, the width of the piezoelectric layer 101 may be 20 micro-meter.

The capacitor may be any type of capacitor known in the art suitable for charge storage purposes in the configuration presented in the present invention. The high K material may be any dielectric material known in the art with high dielectric constant that is used for charge storage purposes. The composite polymers may be any polymers known in the art that comprise materials for electrochemical device applications, such as high energy rechargeable batteries.

Passive layer 104 is a light coat of protective material. Different materials may be used to form this layer such as metal oxide or other similar material that may act to create a shell against corrosion or isolation, which is used to enhance electrical characteristics of the device.

In FIG. 1, the upper harvester is shown to include a piezoelectric thin film layer 105. The thin film piezoelectric layer in the upper harvester may be formed of the same or different material as the piezoelectric material formed in the lower harvester. The piezoelectric thin film layer 105 may be of the same or different thickness than the piezoelectric layer 101 of the lower harvester.

The pressure sensor section of device 100 described in FIG. 1 includes a first metallisation layer 106, a piezoresistive layer 107, an insulating layer 108 and a second metallisation layer 109, all together combined to form a thin film transistor (TFT). A capping layer 110, 410 (in FIG. 4), formed of the same or different material as the passive layer 104, is coupled to the pressure sensor to create a shell against corrosion or isolation which is used to enhance microelectronic devices and system performance. The capping layer 110, 410 (in FIG. 4) is also used for encapsulating the micro-device described in FIG. 1.

FIG. 1 also describes a metal layer 111 formed between the upper and lower harvesters. Metal layer 111 may be formed from any material known in the art that allows the layer to act as the ground between the two harvesters in device 100.

In the pressure sensor section of device 100, the first metallisation layer 106 forms at least a source region 106a and at least a drain region 106b. The piezoresistive thin film layer 107 provides a channel region permitting passage of charge carriers between the source region 106a and the drain region 106b. By way of non-limiting example, the piezoresistive layer 107 may be 4 micro-meter thick and may use germanium. Other suitable material of similar qualities known in the art may be used. In some embodiments, a thin heavily doped layer 107a of microcrystalline silicone of about 0.01 micro-meters may be layered between the piezoresistive layer 107 and the drain and source layer to enhance carrier injection.

Figure 2:
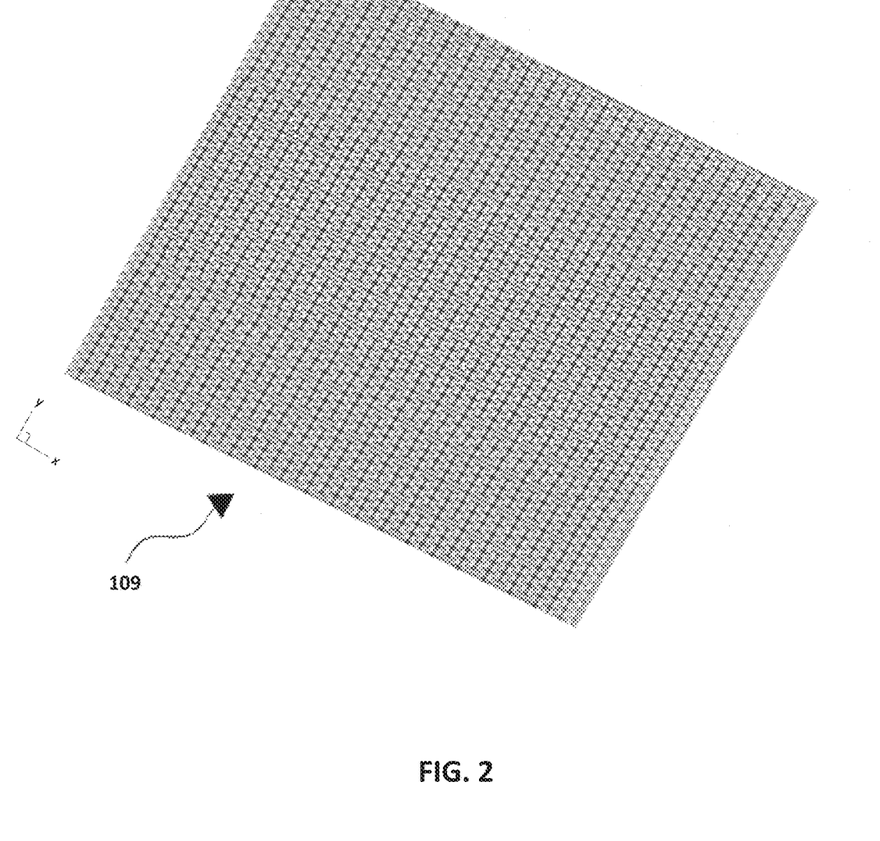
FIG. 2 shows a partial planner view of a gate fractal layer according to an exemplary embodiment of the present invention.

The second metallisation layer 109 forms at least a gate electrode and is deposited between the piezoelectric thin film layer 105 of the upper harvester and the insulator 108 of the pressure sensor. In one exemplary embodiment, the second metallisation layer 109 is deposited as a uniform layer and in this case, the terms second metallisation layer and the gate electrode are used interchangeably. In another embodiment, the gate layer has a fractal layer structure as shown in FIG. 2. The fractal pattern allows for increasing the surface area of the contact area between the gate layer and the piezoelectric thin film layer 105 of the upper harvester. In FIG. 2, the length and width of the different layers may vary depending on the use of the pressure sensor. By way of non-limiting example, the dimensions of the gate layer in FIG. 2 is shown to be 1,000 micro-meter length sides to form a square in its top view and hence the stacked arrangement of the layers in the sensor device would have similar dimensions for this embodiment. As such, the structure of the sensing device described in this embodiment may be described to have 7,300 thin film transistors integrated to comprise the whole sensor. The high number of tft-based pressure sensors may be found to contribute towards increasing the sensitivity of the readings provided by the sensing device.

In some embodiments, the gate fractal layer 109 may be made from platinum as its material. It should be understood that other suitable material known in the art may be used to make the gate fractal layer 109.

The insulating layer 108 is disposed intermediate the piezoresistive thin film layer 107 and the second metallisation layer 109. The insulating nature of layer 108 is used to prevent current from flowing through the piezoresistive layer to the gate electrode 109. By way of non-limiting example, the insulating layer may be made from silicon dioxide with a thickness of 10 micro-meter. It should be understood that other insulating material know in the art may be used to form the insulating layer 108. Also, by way of non-limiting example, the thickness of all fractal layers may be 0.5 micro-meter. However, in some embodiments, the thickness of the fractal layer of the gate layer 109 may be different from that of the first metallisation layer comprising the source region 106a and drain region 106b.

In FIG. 1, the gate electrode 109 is shown to be in electrical communication with the thin film piezoelectric layer 105 of the upper harvester. Piezoelectric thin film layer 105 is also shown to be in electrical communication with the drain region 106b of the pressure sensor through the drain electrode 109 and a conductive metal pad 109a. Furthermore, the source region 106a of the pressure sensor is shown to be in electrical communication with the grounding metal 111. The gate electrode 109 acts as the gate in the device and provides voltage value to the drain region 106b from the upper harvester as will be described in detail below. As the source region 106a is grounded by its electrical connection with grounding metal 111, there will be a voltage difference between the drain region 106b and the source region 106a of the first metallisation layer 106. It should be noted that while in this embodiment, the drain region 106b is shown to be connected to the gate electrode 109 and the source region 106a is shown to be connected to the ground metal 111, the reverse may be possible in other embodiments.

It should be noted that various layers included in the sensing device 100 may be arranged in several different relative positions while still achieving the desired functionality of the device. In all such different arrangements, when considering the pressure sensor and the upper harvester, electrical communication between the piezoelectric layer 105 of the upper harvester will be maintained with one of the drain region 106b or source region 106a. Also, the electrical communication between the grounding metal 111 and the other of the drain region 106b or the source region 106a will be maintained. Furthermore, the positioning of the piezoresistive layer 107 in relation to the drain and source regions, 106a and 106b, respectively, in the first metallisation layer as well as the insulation of the piezoresistive layer 107 from the piezoelectric layer 105 of the upper harvester will be maintained.

Figure 3:
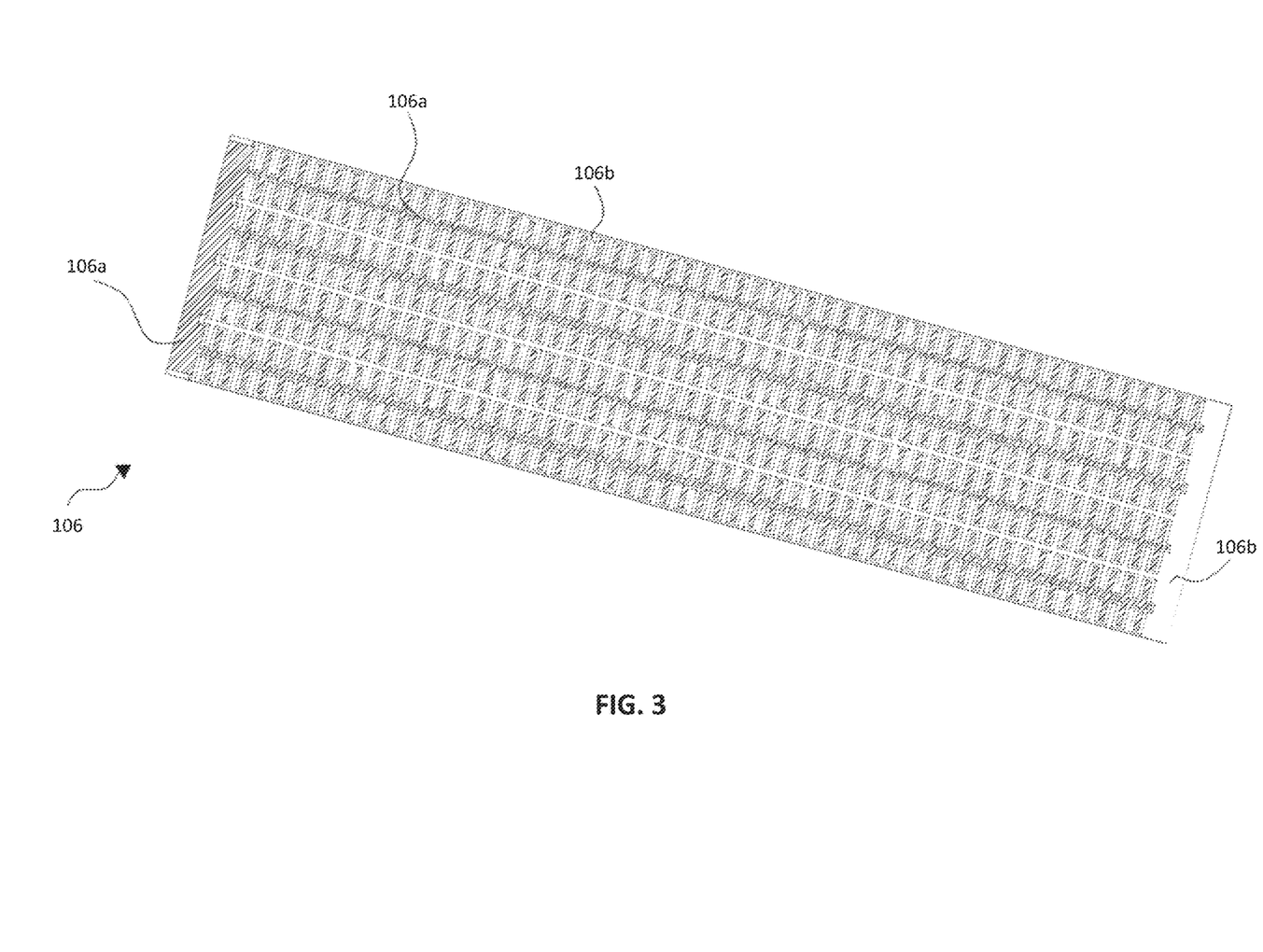
FIG. 3. shows a schematic view of a first metallisation layer representing the source drain regions according to an embodiment of the present invention.
Figure 5:
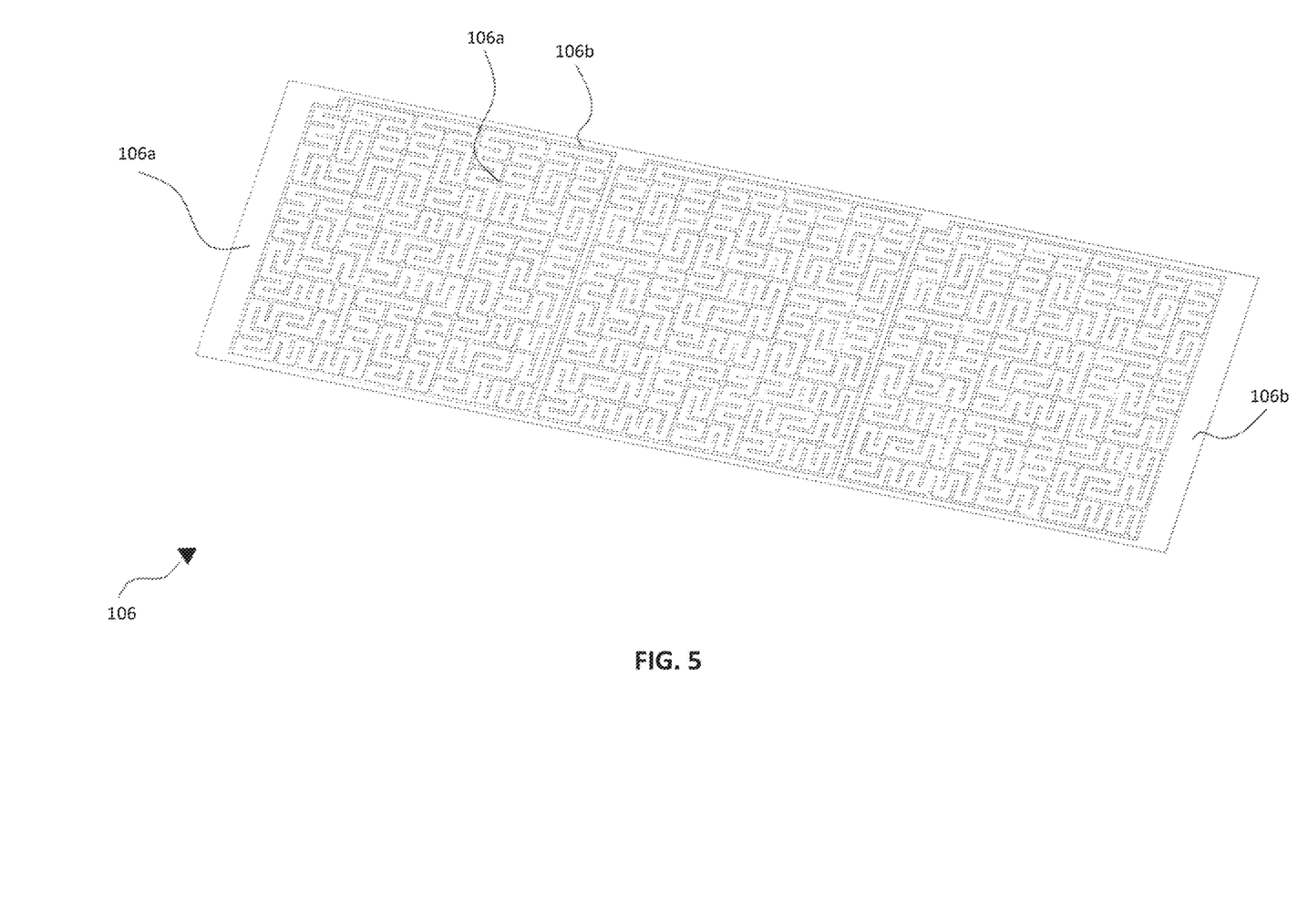
FIG. 5 shows a schematic view of a first metallisation layer representing the source and drain pattern according to another embodiment of the present invention.

As mentioned above, the first metallisation layer 106 is deposited such as to form at least a source region 106a and a drain region 106b. Referring now to FIGS. 3 and 5, a schematic view of a first metallisation layer is illustrated in according with two exemplary embodiments of the present invention.

In one exemplary embodiment of the present invention, the first metallization layer 106 is disposed in such manner as to form an interdigitated structure forming a plurality of pairs of source and drain electrodes 106a, 106b, respectively.

In a further embodiment of the present invention, the first metallization layer 106 is disposed to form a fractal structure forming a plurality of pairs of source and drain electrodes 106a, 106b, respectively.

As will be readily appreciated, interdigitated and fractal arrangements increase an effective surface area between the source region 106a and the drain region 106b across the piezoresistive thin film layer 107 through which electrical current is capable of flowing between the source and drain electrodes 106a, 106b. By way of non-limiting example, the drain and source fractals may be made from gold. Other suitable material known in the art may be used to make the source and drain electrodes 106a and 106b.

When the first metallization layer 106 is disposed to form multiple individual source and drain electrodes 106a, 106b, in the form of interdigitated or fractal structures, an electrical current flowing across the source and the drain regions 106a, 106b is cumulative of individual electrical currents flowing between individual pairs of source and drain electrodes 106a, 106b.

In an exemplary embodiment of the present invention, the source region 106a and the drain region 106b are formed using the same metal. Thus, the source region 106a and the drain region 106b have the same metal function. The source region 106a and the drain region 106b are arranged to form Ohmic contacts with the piezoresistive thin film layer 106. In an alternative embodiment of the present invention, the source region 106a and the drain region 106b are formed using different metals providing different metal functions.

Referring back to FIG. 1, it should be noted that the resistive thin film layer 107 is formed in such manner that the polar axis is substantially orthogonal to a plane along which the piezoresistive thin film layer 107 extends. Thus, in the adjoining figures, the piezoresistive thin film layer 107 extends along the X-Y plane while the polar axis extends along the Z axis. It should also be noted that the piezoelectric layer 105 of the upper harvester is substantially parallel to the piezoresistive layer 107 causing the layers in between them to be substantially parallel to one another.

Figure 4:
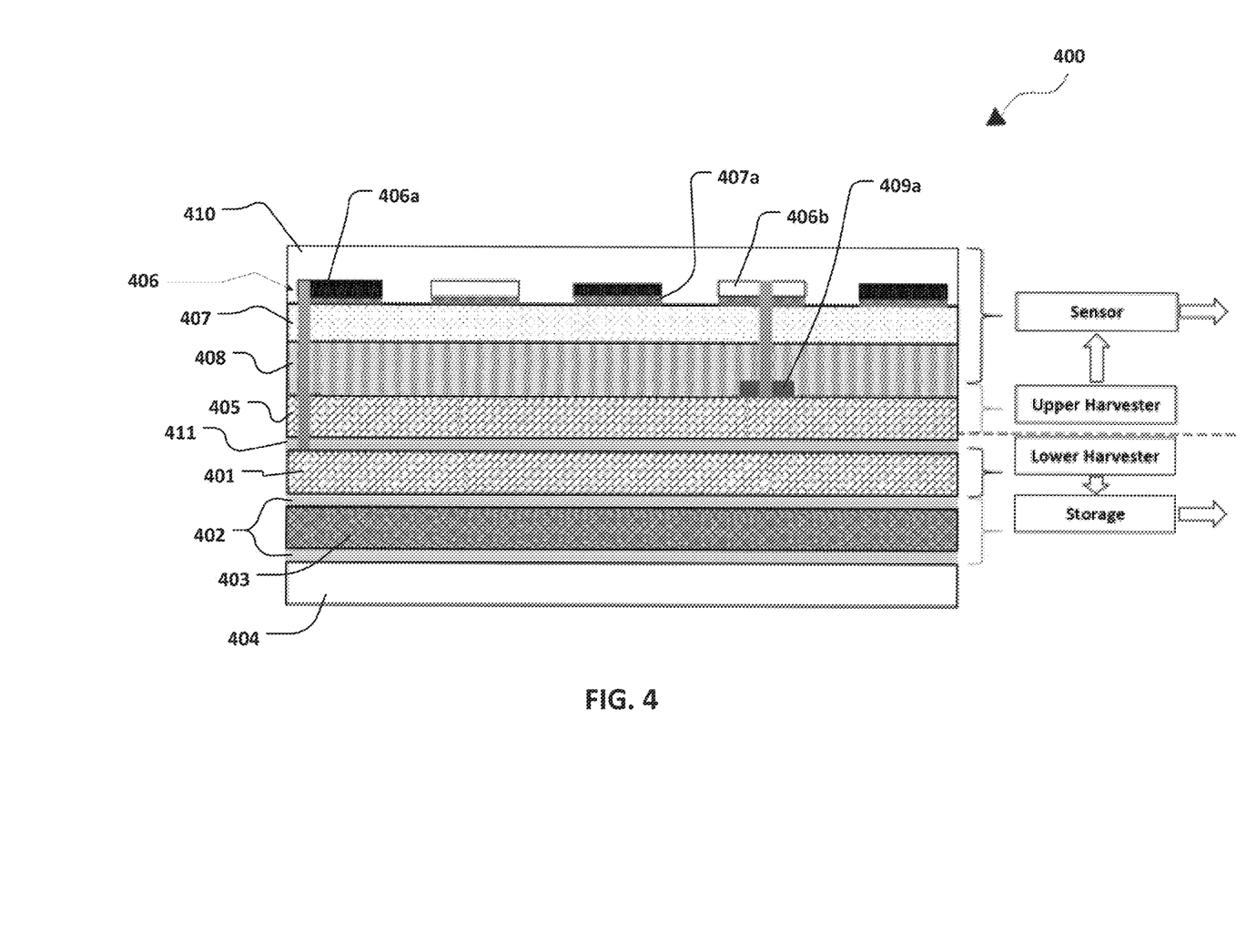
FIG. 4 shows a cross-sectional view of a sensor device according to another example embodiment of the present invention.

Referring to FIG. 4, a cross-sectional view of a sensing device 400 is illustrated in accordance to a second exemplary embodiment of the present invention. This embodiment, is similar to the one described in FIG. 1 with one difference being that the gate fractal layer has been removed to make the gate in the TFT floating. Similar reference numerals have been used in FIG. 4 to correspond to the same elements present in the sensor device presented in FIG. 1. In FIG. 4, the first layer between the piezoelectric and insulating layers acts as the gate for the device.

In operation, the sensor in any of the embodiments described above may be placed on a vibrating object, which will act as the source of the mechanical load applied to the sensing device. When the mechanical load is applied to the device, the piezoelectric thin film layers 101, 401 of the lower harvester will transduce the mechanical energy into electrical energy. The generated electricity will then be transferred to the charge storage unit, where it will be stored for later use when the source of vibration is inactive or is no longer present. It should be noted that the mechanical load may be applied to the top or bottom of the sensing device 100, 400 in order to maximise the surface area to which the mechanical load is applied.

The same mechanical load applied on the device by the source of vibration will also affect the piezoelectric thin film layer 105, 405 of the upper harvester, which will transduce the mechanical load experienced by the upper harvester to electrical energy. The TFT of the device requires voltage to be triggered and voltage for self-biasing. Such voltage is taken from the upper piezoelectric harvester 105, 405 when a vibrating source is present to deliver a mechanical load to the system.

The voltage produced by the piezoelectric thin film 105, 405 of the upper harvester due to the mechanical stress of the vibrating source is internally conducted to the drain region 106b, 406b of the first metallised layer 106, 406 of the pressure sensor section of device 100, 400 through the gate layer and conductive metal pad 109a, 409a, where the gate facilitates regulation of a flow of charge carriers through the piezoelectric thin film layer of the upper harvester. As the source region 106a, 406a of the pressure sensor is electrically internally coupled to the grounding metal 111, 411, the piezoelectric voltage produced by the upper harvester may be measured between the gate electrode and the grounding metal layer. The insulating layer 108, 408 is introduced in order to isolate the gate from the piezoresistive layer 105, 405 and ensure that no current conduction occurs to the gate through the piezoresistive layer 107, 407.

The piezoresistive layer 107, 407 is also affected by the same mechanical load applied to the device 100, 400 due to the source of vibration. This will result in the resistance of piezoresistive layer changing in response to the mechanical load. As the piezoresistive layer 107, 407 is electrically coupled to the drain region 106b, 406b, the voltage generated by the upper piezoelectric harvester is conducted to the piezoresistive layer through the drain region. The generated voltage along with the mechanical properties of the piezoresistive layer results in surface carrier accumulation, bending and lowering of the conduction bond in the piezoresistive layer 107, 407. Said differently, the application of the mechanical load along with the gate voltage and changing resistance in the piezoresistive layer induces current variations between the drain and the source regions within the first metallised layers. Such current values powers the electrical conditional circuits connected to the sensor.

The voltage conducted to the drain region 106b, 406b of the pressure sensor in device 100, 400, causes the sensor to be triggered. As the voltage required for the sensor section of the device to operate is generated only from the mechanical stress applied to the device, the device is then considered as self-biasing. It is noted that as long as a mechanical load continues to apply against the sensor device described, the upper harvester will generate sufficient electrical energy to operate the sensor, which in turn will allow the device to be self-biasing. In the case where the source of vibration is removed or stops vibrating, no mechanical load will be applied to the device and hence, no voltage will be produced from the upper harvester. In such circumstance, the electrical energy stored in the charge storage unit, which was produced using the lower harvester, may be used to bias the device. Electrical coupling between the charge storage unit and the drain region of the pressure sensor will allow for conduction of the electrical energy stored in the storage unit to the drain region of the TFT. Therefore, the self-biasing feature is maintained in the device by the stored electrical energy produced by the lower harvester, at least for a period of time, until such energy is depleted. A control system may be utilised to determine if the source of vibration of the mechanical load has stopped and to allow the transfer of electrical energy from the charge storage unit to the drain region of the pressure sensor. Any control system known in the art may be used to perform such function.

One application of such a self-powered micro-device lies in the medical field as a portable and flexible cardiac cycle monitor that utilizes a combination of piezoelectric and piezoresistive materials to provide remote, unobtrusiveness and continuous patient observation during prolonged treatment. There is a worldwide increase in the number of patients suffering from cardiovascular diseases (CVD). Cases that go undetected in the early stage introduce a delay in medication causing the heart disease to advance to a level where it is difficult to cure. Due to the high sensitivity, small size, light weight, lower external power consumption and cost efficiency in making the sensor device described in this current disclosure, such device may be utilized in constructing a portable self-biasing, long term monitoring systems that can detect CVD in its early stages using heart signals as the mechanical load on the device.

Mechanical movement on the surface of a body of a human is caused, at least in part, by mechanical movement of the human's internal organs such as heart muscles, lungs and other organs. The current disclosure may refer hereinafter to the activity of internal organs in a human, a person or a subject; however, it is to be understood that the teachings in this disclosure covers activity of any moving organ in any living organism.

When piezoelectric material is attached to the person's body, the mechanical movement of the body models a mechanical load and produces a relative induced strain on the piezoelectric material, which in turn causes the piezoelectric material to generate a voltage corresponding to heartbeats of the person, which in turn is used to obtain the person's cardiac cycle. U.S. patent application Ser. No. 15/095,956, entitled "Apparatus and Method for Physiological Mechanical and Electrical Activity Monitoring" describes in detail a technique used to model the cardiac activity of a person using the piezoelectric effect. The entire content of that application is hereby incorporated by reference.

In operation, the device described in the present invention may be placed on a flexible sheet, which may be placed directly onto a body part of the person, such as the chest area. Alternatively, the sensing device may be placed directly onto the body part of the person. The flexible sheet may be made from different suitable material known in the art that are compatible with electronic processing. The flexible sheet permits deformation of the stack of various layers in the sensing device including the lower harvester, the upper harvester and the piezoresistive layer in the pressure sensor.

The heartbeat of the person will contribute the mechanical load required to operate the device as described above. Through the operation of the lower harvester, upper harvester and the pressure sensor in the device, the device produces an output current and voltage, which are proportional to the heart muscle movements, which may be used to extract heart pressure parameters and the cardiac cycle monitoring. These two parameters count as the output of the self-powered nano-device of the present invention.

It should be noted that when the device of the present invention is applied for the cardiac monitoring of the person, the mechanical load applied on the device corresponds to movement of the chest cause due to the internal movement of the heart of the person, among other internal organs. Therefore, as long as the person has a beating heart, the movement of the person's chest will be continuous. Therefore, the upper harvester will continue to produce voltage as long as the device is coupled to the person's chest. In such case, the energy generated by the lower harvester may not be required to trigger the TFT of the sensor device.

Therefore, in some embodiments, the sensor device of the present invention may not comprise the lower harvester and storage unit where the sensor is used for monitoring cardiac activity of a person. Similarly, the harvester may not be present in embodiments, where the sensor device is applied on a source of continuous mechanical motion. In such circumstances, the continuous mechanical load may cause the upper harvester to continuously produce electrical energy, which may be used to trigger the TFT of the sensor device and allow it to operate.

It should also be noted that where the lower harvester is included in the sensor device, the stored electrical energy produced by the lower harvester may be used for triggering and operating other devices different from the TFT of the sensor device.

As provided above, the piezoelectric harvesters convert mechanical energy from load impact to electrical energy. The applied stress T could be found from the force F, which causes electric energy to be generated by piezoelectric conversion under compression of the force F and the area A of the piezoelectric harvester according to the following formula:

$$T = \frac{F}{A} \quad (1)$$

The induced polarization equals:

$$P = d_{33}T \quad (2)$$

where P is the induced polarization, T is the stress that is applied in the direction of the thickness t and $d_{33}$ is the piezoelectric constant along t.

Based on the above equations, the polarization charge Q may be found from the following formula:

$$Q = PA \quad (3)$$

Equations (2) and (3) may be manipulated to get:

$$Q = d_{33}TA \quad (4)$$

From equation (1), the relation between the force and the stress is substituted into equation (4) to get:

$$Q = d_{33}F \quad (5)$$

The capacitance C of the piezoelectric element equals:

$$C = \frac{\varepsilon_o \varepsilon_r A}{t} \quad (6)$$

where $\varepsilon_o$ is the permittivity of vacuum and $\varepsilon_r$ is the permittivity of material.

Thus, the voltage induced V may be calculated using:

$$V = \frac{Q}{C} \quad (7)$$

By substituting the formulas of the charge and the capacitance from equations (5) and (6) into equation (7) the following may be obtained:

$$V = \frac{d_{33}Ft}{\varepsilon_o \varepsilon_r A} \quad (8)$$

The constant d and the piezoelectric voltage rate g are fixed by the material and has the following relation:

$$g = \frac{d_{33}}{\varepsilon_o \varepsilon_r} \quad (9)$$

From formula (9), the voltage may be found using:

$$V = \frac{gFt}{A} \quad (10)$$

The generated energy E from the piezoelectric material in equation (11) may be found from equation (12) using formulas (6) and (9):

$$E = \frac{1}{2}CV^2 \quad (11)$$

$$E = \frac{d_{33}gF^2 t}{2A} \quad (12)$$

where C is the capacitance of the piezoelectric element and V is the voltage.

In the piezoresistive layer, the sensitivity of a piezoresistive sensor is calculated using the following equation:

$$\frac{\Delta R}{R} = F\left(\frac{12\pi_l l(t - t_s)}{wt^3}\right) \quad (13)$$

where l is the length, w is the width, and t is the thickness.

The gauge factor (GF) is defined as the ratio of the change in the resistance to mechanical stress applied on the sensor as shown in equation (14). It may be seen that the sensitivity is proportionally related to the strain.

$$GF = \frac{\left(\frac{\Delta R}{R}\right)}{\left(\frac{\Delta L}{L}\right)} \quad (14)$$

The strain is found from the stress that is defined in equation (1) using the following equation:

$$\frac{\Delta L}{L} = \frac{F}{EA} \quad (15)$$

where L is the length and R is the resistance.

From equations (14) and (15), the sensitivity may be calculated using the following:

$$\frac{\Delta R}{R} = GF\left(\frac{F}{EA}\right) \quad (16)$$

FIGS. 6-11 show a computer simulation and results for the model provided above using the software Coventorware™. The simulation was provided in two steps—the piezoelectric simulation and the piezoresistive simulation. The simulation was conducted assuming the contacts to be Ohmic. The piezoelectric simulation was conducted first, with a range of forces being applied to the grounded bottom gold plate of the device as shown in FIG. 1. The result of the simulation was the corresponding voltage generated at the gate fractal of the device, which was a result of the piezoelectric effect—applied mechanical stress leading to generation of voltage. The generated voltage versus applied force graph was obtained to be non-linear, and was a good measure of the piezoelectric material's response of the device.

The piezoresistive simulation involved using the mechanical deformation caused by the applied force as well as the voltage generated by the piezoelectric layer as the inputs. With the source fractal being grounded, the voltage and the resistance between the drain and the source fractals was measured and current was calculated using the data obtained. The current versus voltage characteristic was plotted as a result and the graph was found to be linear. The negative side of the current voltage characteristic is obtained by exerting a downward pulling force on the bottom plate of the device instead of the upward push force applied to obtain the positive curve. The negative voltage and current characteristic is also found to be linear.

Figure 6:
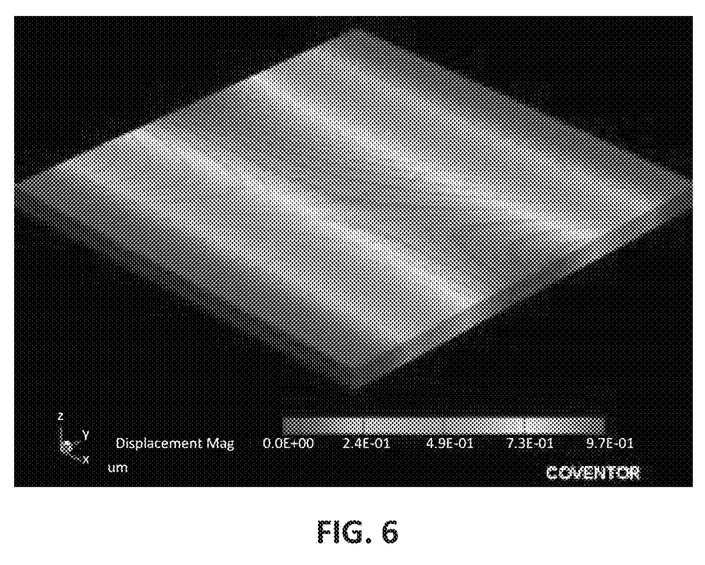
FIG. 6 shows the displacement results of the Coventorware™ computer simulation for an applied force of 500 $e^{-3}$ $uN/um^2$.

Along with plotting the generated voltage corresponding to variations in applied force as well as the output current versus the generated voltage, the mechanical displacement in accordance to the applied force is also measured. FIG. 6 shows the displacement results of the Coventorware™ simulation for an applied force of 500 $e^{-3}$ micro-newton per micrometer-square. The maximum displacement is noted as 0.97 micrometer.

Figure 7:
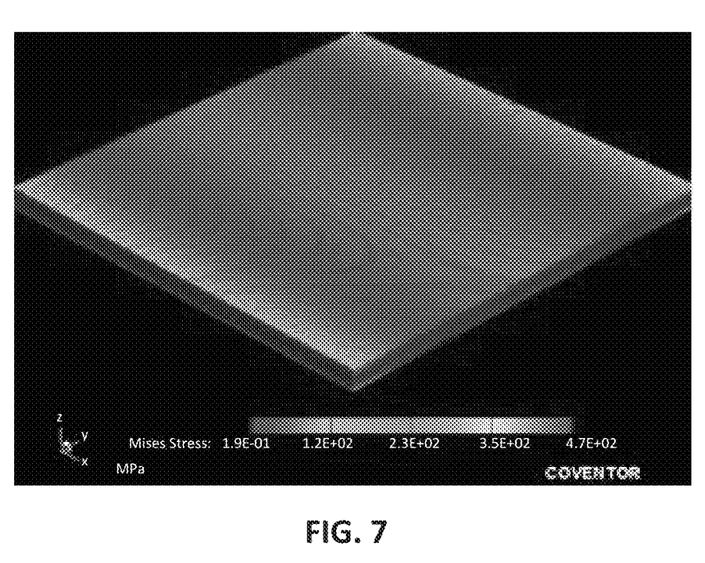
FIGS. 7 and 8 show the Mises stress distribution on the topmost layer and the bottom piezoelectric layer of the device in FIG. 1, respectively.
Figure 8:
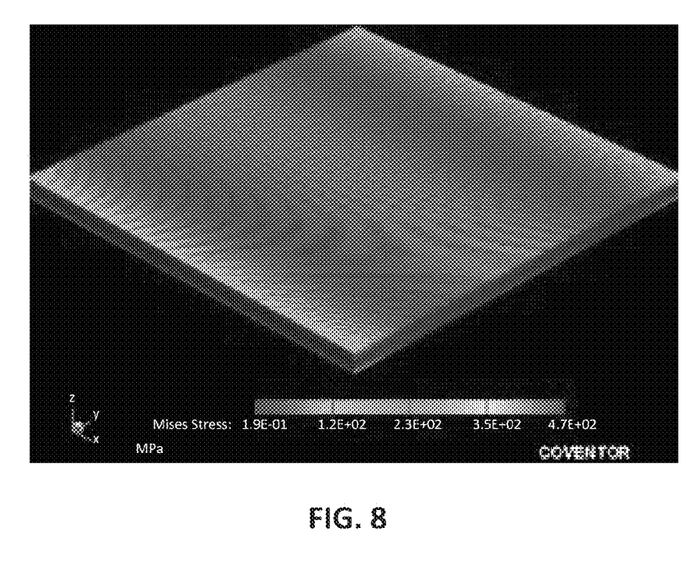

The Mises stress developed on different layers of the device upon application of force are also mapped. FIGS. 7 and 8 show the Mises stress distribution on the topmost layer and the bottom piezoelectric layer of the device of FIG. 1, respectively.

Figure 9:
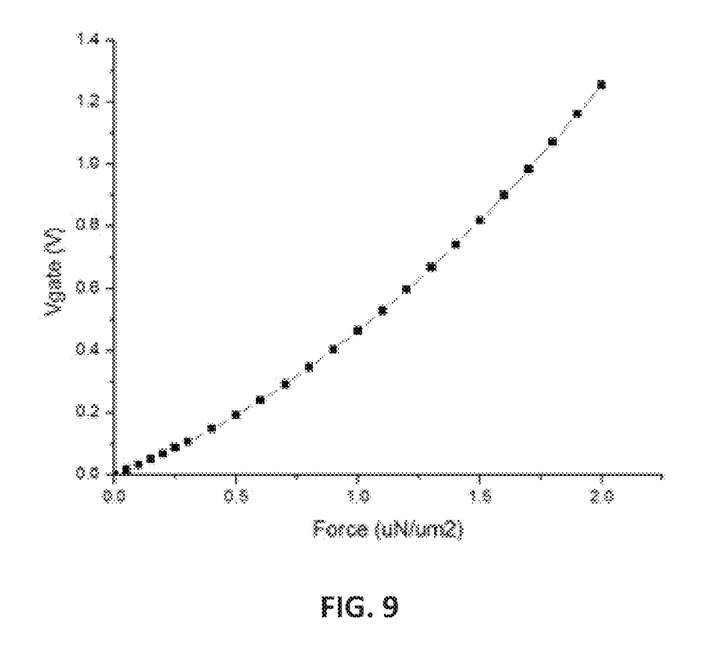
FIG. 9 shows the plot of the voltage generated by the piezoelectric component of the device of FIG. 1 corresponding to the applied force.

In relation to the Voltage Force characteristics, the graph in FIG. 9 shows the plot of the voltage generated by the piezoelectric component of the device corresponding to the applied force. The generated voltage is utilised as the gate voltage of the device. The applied force is varied from a range of 1e-3 to 2 micro-newton per micrometer-square.

Figure 10:
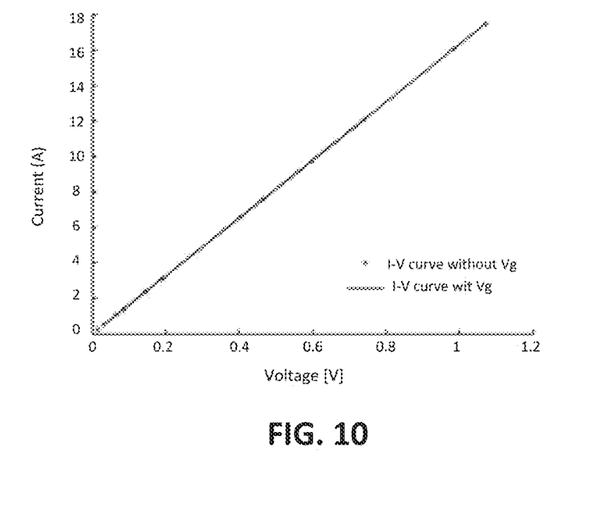
FIG. 10 shows the current component of the device in FIG. 1 in response to the applied gate voltage as generated by the piezoelectric component in both cases, with and without the existence of gate voltage (Vg).

In relation to Current Voltage characteristic, the graph in FIG. 10 shows the current component of the device in response to the applied gate voltage as generated by the piezoelectric component in both cases, with and without the existence of gate voltage (Vg).

Figure 11:
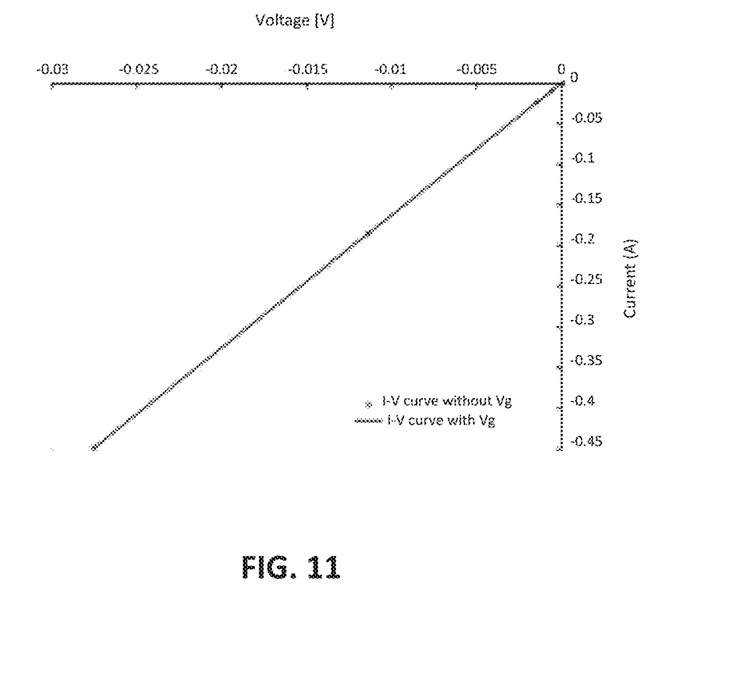
FIG. 11 shows the negative current-voltage characteristic obtained upon changing the direction of the applied force from upward to downward in both cases, with and without the existence of gate voltage (Vg).

FIG. 11 shows the negative current-voltage characteristic obtained upon changing the direction of the applied force from upward to downward in both cases, with and without the existence of gate voltage (Vg).

As seen from the figures, the simulation results confirmed that the combination of the piezoelectric and piezoresistive components in the device worked in conjunction to respond to the applied force by generating an output voltage and current. A voltage generated by the piezoelectric component was noted upon application of external force, varying proportionally with variations in the applied force. The generated voltage served as the applied gate voltage for the piezoresistive component of the device. An output voltage and current were noted between the drain and the source plates of the piezoresistive layer. A linear characteristic for the I-V curve was obtained.

Thus, in accordance with the device and method described in the present invention, the sensing device advantageously provides improved sensitivity to application of external force thereto.

The sensing device of the present invention is considered to have a low energy cost given the self-biasing nature of the device, which results from the piezoelectric effect that allows the sensing device to harvest waste mechanical energy from the surrounding environment of the device to transduce it into usable electrical energy to power the device.

Owing to its small size, light weight, as well as the lack of need for external and obtrusive wiring, the sensing device may be suitable for use for sensing application in wearable devices that require sensing functionality. As a sensor, the sensing device has potential applications in many fields including but not limited to the medical and biomedical fields and particularly in long term monitoring of cardiac activity. Such sensing devices may allow for the person to monitor his or her cardiac activity. It may also allow for the remote monitoring of the person's cardiac activity by a third party such as a doctor, health centre or a hospital.

Interpretation of Terms

Unless the context clearly requires otherwise, throughout the description and the claims:

"comprise," "comprising," and the like are to be construed in an inclusive sense, as opposed to an exclusive or exhaustive sense; that is to say, in the sense of "including, but not limited to".

"connected," "coupled," or any variant thereof, means any connection or coupling, either direct or indirect, between two or more elements; the coupling or connection between the elements can be physical, logical, or a combination thereof.

"herein," "above," "below," and words of similar import, when used to describe this specification shall refer to this specification as a whole and not to any particular portions of this specification.

"or," in reference to a list of two or more items, covers all of the following interpretations of the word: any of the items in the list, all of the items in the list, and any combination of the items in the list.

the singular forms "a", "an" and "the" also include the meaning of any appropriate plural forms.

"subject" refers to a human or other animal. It is intended that the term encompass patients, such as vocally-impaired patients, as well as inpatients or outpatients with which the present invention is used as a diagnostic or monitoring device. It is also intended that the present invention be used with healthy subjects (i.e., humans and other animals that are not vocallly-impaired, nor suffering from disease). Further, it is not intended that the term be limited to any particular type or group of humans or other animals.

"transducer" refers to any device that converts a non-electrical parameter (e.g., sound, pressure or light), into electrical signals or vice versa. Microphones are one electroacoustic transducers.

"power source" and "power supply" refer to any source of electrical power in a form that is suitable for operating electronic circuits.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", "upper", "lower" and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

Where a component (e.g. a circuit, module, assembly, device, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of device and method have been described herein for purposes of illustration. These are only examples. The technology provided herein can be applied to device and method other than the examples described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions and sub-combinations as may reasonably be inferred. The scope of the claims should not be limited by the preferred embodiments set forth in the examples, but should be given the broadest interpretation consistent with the description as a whole.

What is claimed is:

1. A self-biasing sensor comprising:
   an upper harvester having a piezoelectric thin film layer; and
   a pressure sensor comprising:
      a first metallization layer forming at least a drain region and a source region;
      a piezoresistive thin film layer for providing a channel region permitting passage of charge carriers between the source region and the drain region;
      a second metallization layer forming a gate electrode, the gate electrode in electrical communication with the piezoelectric thin film layer of the upper harvester; and
      an insulator disposed intermediate the piezoresistive thin film layer and the second metallization layer, the insulator insulating the piezoresistive thin film layer from the second metallization layer,
   wherein the gate electrode is in electrical communication with one of the drain region and the source region and the other one of the drain region and the source region is grounded, and wherein the gate electrode facilitates regulation of flow of charge carriers through the piezoelectric thin film layer of the upper harvester, and wherein the flow of charge carriers is modulated in response to a strain in the piezoelectric thin film layer.

2. The self-biasing sensor of claim 1, wherein the piezoelectric thin film layer of the upper harvester is in a plane substantially perpendicular to a direction of the applied stress on the self-biasing sensor and wherein the first metallization layer and the second metallization layer are substantially parallel to the piezoelectric thin film layer of the upper harvester.

3. The self-biasing sensor according to claim 1, the self-biasing sensor further comprising: a lower harvester having a piezoelectric thin firm layer for harvesting electrical energy in response to a strain in the piezoelectric thin film layer of the lower harvester and storing the harvested electrical energy in an energy storage unit.

4. The self-biasing sensor according to claim 3, wherein the lower harvester and the upper harvester are disposed substantially parallel to one another and to a plane substantially perpendicular to a direction of the applied strain on the self-biasing sensor.

5. The self-biasing sensor according to claim 1, wherein the first metallization layer is disposed to form an interdigitated structure forming a plurality of pairs of source and drain electrodes.

6. The self-biasing sensor according to claim 5, wherein an electrical current flowing across the source and the drain electrodes is cumulative of individual electrical currents flowing between individual pairs of source and drain electrodes.

7. The self-biasing sensor according to claim 1, wherein the first metallization layer is disposed to form a fractal structure forming a plurality of pairs of source and drain electrodes.

8. The self-biasing sensor according to claim 7, wherein an electrical current flowing across the source and the drain electrodes is cumulative of individual electrical currents flowing between individual pairs of source and drain electrodes.

9. The self-biasing sensor according to claim 1, wherein the second metallisation layer is disposed to form a fractal structure of the gate electrode.

10. The self-biasing sensor according to claim 1, wherein the gate electrode of the second metallisation layer is a floating gate.

11. The self-biasing sensor according to claim 1, wherein the source region and the drain region are arranged to form Ohmic contacts with the piezoresistive thin film layer of the upper harvester.

12. A method of forming a self-biasing sensor, the method comprising the steps of:
    providing an upper harvester forming a piezoelectric thin film layer;
    providing a first metallization layer forming at least a source region and at least a drain region;
    providing a piezoresistive thin film layer as a channel region permitting passage of charge carriers between the source region and the drain region;
    providing a second metallization layer forming a gate electrode, the gate electrode in electrical communication with the piezoelectric thin film layer of the upper harvester;
    providing an insulator disposed intermediate the piezoresistive thin film layer and the second metallization layer;
    wherein the first metallization layer, the piezoresistive thin film layer, the second metallization layer and the insulator are vertically integrated to form a pressure sensor and wherein the gate electrode facilitates regulation of a flow of charge carriers through the piezoelectric thin film layer of the upper harvester, and wherein the flow of charge carriers is modulated in response to a strain in the piezoelectric thin film layer of the upper harvester.

13. The method according to claim 12, the method further comprising: providing a lower harvester having a piezoelectric thin film layer for harvesting electrical energy in response to a strain in the piezoelectric thin film layer of the lower harvester and storing the harvested electrical energy in an energy storage unit.

14. The method according to claim 13, wherein the source region and the drain region are coplanar, the piezoelectric thin film layer is substantially perpendicular to an axis along which the strain is applied, and wherein both the pressure sensor and the piezoelectric thin film layer of the lower harvester are substantially parallel to the piezoelectric thin film of the upper harvester.

15. The method of operating a self-biased sensor, the self-biasing sensor comprising: an upper harvester having a piezoelectric thin film layer; and a pressure sensor comprising: a first metallization layer forming at least a drain region and a source region; a piezoresistive thin film layer for providing a channel region permitting passage of charge carriers between the source region and the drain region; a second metallization layer forming a gate electrode, the gate electrode in electrical communication with the piezoelectric thin film layer of the upper harvester; and an insulator disposed intermediate the piezoresistive thin film layer and the second metallization layer, the insulator insulating the piezoresistive thin film layer from the second metallization layer, the gate electrode is in electrical communication with one of the drain region and the source region and the other one of the drain region and the source region is grounded, and the gate electrode facilitates regulation of a flow of charge carriers through the piezoelectric thin film layer of the upper harvester, and the flow of charge carriers is modulated in response to a strain in the piezoelectric thin film layer, the method comprising the steps of:

coupling a source of mechanical load to the self-biasing sensor, and applying a mechanical stress to the self-biasing sensor using the source of mechanical load, the mechanical stress affecting the piezoelectric layer of the upper harvester and the piezoresistive layer of the pressure sensor; and     generating an output current and voltage based on the applied mechanical stress,     wherein the generated output current and voltage are sufficient to operate the self-biased sensor without use of an external power source.

16. The method of claim 15, wherein the mechanical stress is associated with mechanical movement of a part of a person's body resulting from at least cardiac activity of the person and wherein the method further comprises monitoring the cardiac activity of the person based on the generated output current and voltage.

17. The method according to claim 15, the method further comprising: providing a lower harvester having a piezoelectric thin firm layer for harvesting electrical energy in response to a strain in the piezoelectric thin film layer of the lower harvester caused by the mechanical stress.

18. The method according to claim 17, the method further comprising orienting the lower harvester and the upper harvester to be disposed substantially parallel to one another and to a plane substantially perpendicular to a direction of the applied strain.

19. The method of claim 18, the method further comprising storing the harvested electrical energy in an energy storage unit.

20. The method of claim 19, the method further comprising: using the electrical energy stored in the energy storage unit to trigger the pressure sensor and wherein the output current and voltage generated are based at least in part on the electrical energy used.

* * * * *

UNITED STATES PATENT AND TRADEMARK OFFICE
CERTIFICATE OF CORRECTION

PATENT NO. : 10,401,139 B2
APPLICATION NO. : 15/403042
DATED : September 3, 2019
INVENTOR(S) : Al Ahmad et al.

It is certified that error appears in the above-identified patent and that said Letters Patent is hereby corrected as shown below:

On the Title Page

Item (72), delete inventor name "Areen Abdellah Romi Allataifeh" and insert -- Areen Abdallah Romi Allataifeh --.

Signed and Sealed this
Tenth Day of December, 2019

Andrei Iancu
*Director of the United States Patent and Trademark Office*